United States Patent [19]

Fried

[11] 4,018,820
[45] Apr. 19, 1977

[54] CHEMICAL SYNTHESIS
[75] Inventor: Josef Fried, Chicago, Ill.
[73] Assignee: The University of Chicago, Chicago, Ill.
[22] Filed: Sept. 5, 1974
[21] Appl. No.: 503,215

Related U.S. Application Data

[63] Continuation-in-part of Ser. No. 274,365, July 24, 1972, abandoned, and Ser. No. 400,297, Sept. 24, 1973, abandoned, which is a continuation of Ser. No. 361,664, May 18, 1973, abandoned, which is a continuation of Ser. No. 53,663, July 9, 1970, abandoned.

[52] U.S. Cl. .................. 260/514 D; 260/448.2 R; 260/457; 260/468 D; 260/470; 260/488 R; 260/514 J; 260/516; 260/609 F; 424/305; 424/317
[51] Int. Cl.² ........................................ C07C 177/00
[58] Field of Search .................. 260/468 D, 514 J

[56] References Cited
OTHER PUBLICATIONS

Fried, et al., Ann. N.Y., Acad. of Sci., 180 41(1971).
Burger, *Medicinal Chemistry*, 2nd Ed. p. 77, (1960).

Primary Examiner—Robert Gerstl

[57] ABSTRACT

This invention relates to pharmacologically active compounds of the formula:

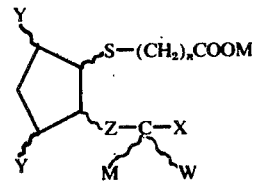

wherein
 Z is trans-CH=CH, C≡C; or $CH_2$-$CH_2$;
 M is H or lower alkyl;
 n is an integer of from 2 to 5;
 X is alkyl;
 W is H or OR, wherein R is H, acyl, or alkyl; and
 each Y is H, OH or alkoxy;
and to novel intermediates and processes useful in the production thereof.

4 Claims, No Drawings

CHEMICAL SYNTHESIS

The invention described herein was made in the course of work done under a grant from the United States Department of Health, Education and Welfare.

This application is a continuation in part of my prior filed copending applications, Ser. No. 274365, filed July 24, 1972 and Ser. No. 400,297 filed Sept. 24, 1973, which in turn is a continuation application of my prior filed copending application Ser. No. 361,664, filed May 18, 1973, which in turn is a continuation application of my prior filed application Ser. No. 53663, filed July 9, 1970, all now abandoned.

This invention relates to and has as its objective the production of novel pharmacologically active compounds of the formula:

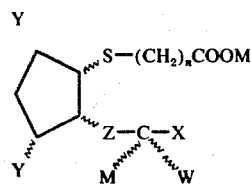

wherein
Z is trans. —CH=CH, C ≡ C or $CH_2$—$CH_2$;
M is H or lower alkyl;
N is an integer of from 2 to 5;
X is alkyl;
W is H or OR, wherein R is H, acyl or alkyl; and each Y is H, OH, acyloxy or alkoxy;
and to novel intermediates and processes useful in the production thereof.

More particularly, this invention relates to the production and use of compounds which possess physiological properties and possess the formulae:

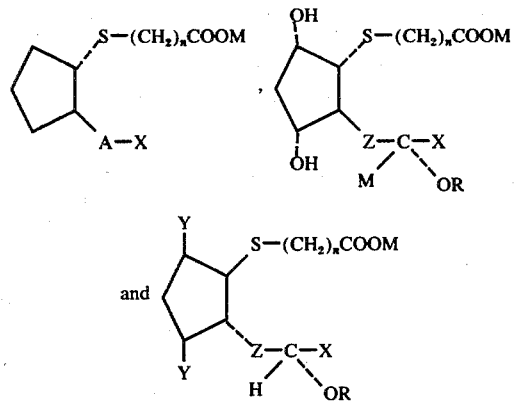

wherein
A is CH=CH or $CH_2$—$CH_2$
R is H, acyl or lower alkyl;
X is alkyl or from 4 to 10 carbon atoms; and
Y is hydroxy, acyloxy or lower alkoxy;
Z, M, X and n are as defined hereinabove.

In the most preferable embodiments of the instant invention it has been found that most satisfactory results are obtained with the compounds of this invention, as set forth in the above formulae, wherein:
A is trans. CH=CH;
Z is trans. CH=CH or C ≡ C;
M is hydrogen or methyl;
n is an integer of from 2 to 5;
X is alkyl of less than 8 carbon atoms;
R is hydrogen, acetyl or methyl; and
Y is hydroxy; acetoxy or methoxy.

The preferred acyl or acyloxy radicals of this invention are those derived from hydrocarbon carboxylic acids of twelve carbon atoms or less and include such acids as the lower alkanoic acids, for example, acetic or propionic acids, the lower alkenoic acids, the monocyclic aryl carboxylic acids for example, benzoic and toluic acids, the monocyclic aryl lower alkanoic acids, for example, phenylacetic and β-phenylpropionic acids, the cycloalkane carboxylic acids and the cycloalkene carboxylic acids.

Whenever in the formulae set forth in this specification and the claims appended hereto, a curved line ($) is employed in the linkage of atoms it is intended to denote that the connected atom may be either in the β or α position, that is, either above or below the plane of the paper as is determined in each of the respective compounds involved.

The final products of this invention are physiologically active compounds possessing prostaglandin-like activity. Thus, the final products of this invention may be administered to patients for the purpose of causing the contraction of smooth muscles, such as the smooth muscles of the uterus. The final products of this invention may therefore be employed for the purpose of inducing labor or abortions in pregnant patients to whom they are administered.

In addition, it has been found that some of the final products of this invention have the ability to cause regression of the corpus luteum in mammals and can therefore be employed for such purposes as estrus synchronization in domestic animals, thereby achieving a greater economy and efficiency in the practice of artificial insemination of domestic animals.

Further to the foregoing, certain of the final products of this invention act as bronchodilators and can therefore be employed in the treatment of such medical conditions as bronchial asthma. It has also been found that some of the final products of this invention act as inhibitors of the secretion of gastric acids and pepsin in mammals and can therefore be employed in the prevention or therapeutic treatment of such conditions, for example, duodenal ulcers.

Furthermore, it has been found that certain of the final products of this invention show antiprostaglandin action, that is, they inhibit the action of prostaglandins either formed in the body or of prostanoids administered externally. Actions that may be inhibited are such physiological actions that are mediated by the natural prostaglandins or by synthetic prostanoids. Such activities as can be inhibited include excessive stimulation of smooth muscles such as the uterus or the intestines. Thus, certain compounds of this invention can therefore be employed in the treatment of various kinds of diarrhea including such caused by bacteria, e.g. vibro cholerae. They can also be used as antiinflammatory agents or to inhibit excessive secretion of certain endocrine glands, such as the thyroid gland, the adrenal cortex and the pituitary gland.

It has also been determined that certain of the final products of this invention are resistant to the action of the major prostaglandin inactivating enzyme, i.e. prostaglandin 15-dehydrogenase. In fact, it appears that these compounds may serve as inhibitors of this inactivating enzyme, which has the effect of prolonging and enhancing the physiological activity of these products in the body, especially in comparison to naturally occurring prostaglandin compounds.

The final pharmacologically active compounds of this invention may be administered to the mammal being treated hereunder, in any manner known and convenient to the skilled worker practicing the invention, the dosage and concentration of the final product being adjusted for the requirements of the patient and the properties of the respective final product being employed. The skilled worker can prepare the final products in such compositions and dosage forms as are usually employed for such purposes, depending upon the route of administration selected for the ultimate composition, for example, parenteral, peroral, or topical final dosage forms and administration routes.

The final products of this invention are prepared by the processes of this invention which entail a number of steps, beginning with a cyclopentyl epoxide as the starting material. The steps involved in the processes of this invention may be generally represented by the following equations:

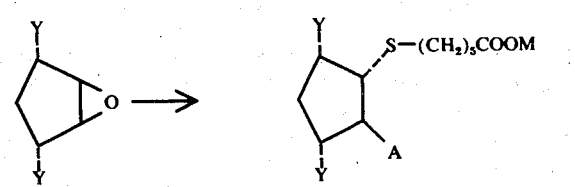

I.
a. Y=H
b. Y=O Benzyl

II.
a. Y=H; M=CH$_3$; A=OH
b. Y=H; M=H; A=OH
c. Y=H; M=H; A=Cl
d. Y=H; M=H; A=Br
e. Y=O Benzyl; M=CH$_3$; A=OH
f. Y=O Benzyl; M=H; A=OH
g. Y=O Benzyl; M=H; A=Cl
h. Y=O Benzyl; M=H; A=Br

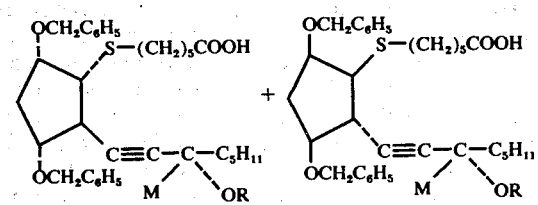

III.
a. R=t-butyl; M=H
b. R=trimethylsilyl; M=H
c. R=H; M=CH$_3$
d. R=t-butyl; M=CH$_3$
e. R=trimethylsilyl; M=CH$_3$

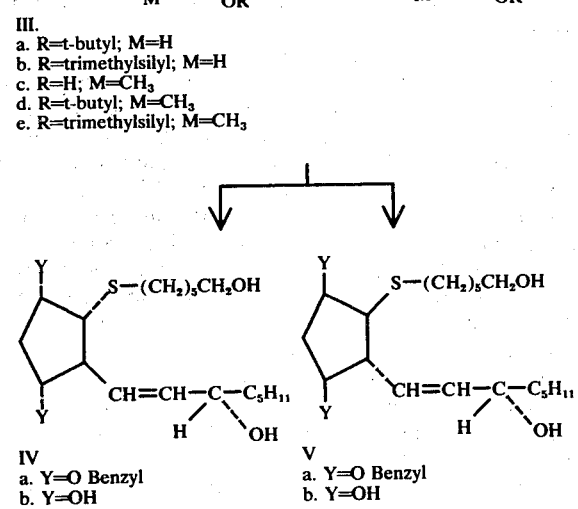

IV
a. Y=O Benzyl
b. Y=OH

V
a. Y=O Benzyl
b. Y=OH

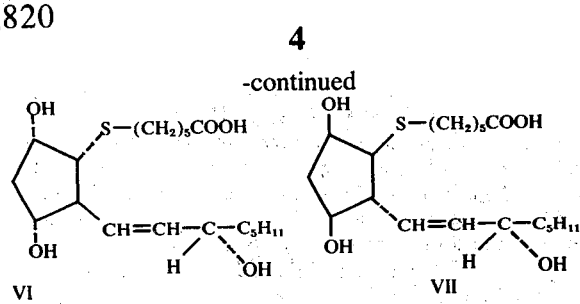

VI

VII

The epoxide starting material (Compounds I) may be prepared in accordance with the teachings of my prior filed application Ser. No. 274365, filed July 24, 1972. Compounds I are then converted by treatment with an alkylmercapto alkanoate, for example, methyl 6-mercapto-n-hexanoate, ethyl 5-mercapto-n-pentanoate, or methyl 4-mercapto-n-butanoate, in the presence of an alkali metal alkoxide, for example sodium methoxide, to yield the respective hydroxy alkyl esters of Compound II which are new compounds of this invention. These alkyl esters may then be hydrolyzed as by treatment with an alcoholic alkali metal base, for example, methanolic KOH, to yield the corresponding free acids of Compounds II, which are also new compounds of this invention. These free acid compounds may then be treated with an alkane sulfonyl halide, for example methanesulfonyl chloride, in an organic base medium, for example, pyridine to yield the halosubstituted free acids of Compounds II, which are also new compounds of the instant invention. These halo-substituted free acids, may then be converted to other halo-substituted acids, for example, bromo-substituted acids, by treatment with lithium halide, for example, lithium bromide or lithium iodide, in dimethoxyethane, to yield the corresponding halide substituted acids of Compounds II, may then be treated with an alkoxy-alkynyl lithium reagent, for example, butoxy-octynyllithium, butoxy-heptynyl lithium or butoxy-hexynyl lithium and more particularly, (S) 3-t-butoxy-1-octynyllithium, 3-t-butoxy-1-heptynyllithium, or 3-t-butoxy-1-hexynyllithium, in dimethoxyethane to yield after esterification with an esterification agent such as diazomethane the acetylenic compounds of Compounds III, which are new compounds of this invention. The free hydroxy ester of Compounds III may then be obtained by de-t-butylation, for example, by treatment with trifluoroacetic acid. These free hydroxy esters may then be reduced, as by treatment with a reducing agent, such as lithium aluminum hydride in tetrahydrofuran to yield a racemic mixture of the diastereomer of Compounds IV and V, which may then be separated into the individual compounds, for example, by chromatographic methods, which are also new compounds of this invention. Each of these separated members of Compounds IV and V may then be debenzylated by conversion into the dianion by treatment with sodium hydride in tetrahydrofuran, followed by reduction with lithium in ammonia in tetrahydrofuran to form the corresponding tetrol compounds of Compounds IV and V, which are also new compounds of this invention. These tetrol compounds are then selectively oxidized for example, with platinum oxide in sodium bicarbonate in water-acetone to form the respective 7-thia PGF$_{1\alpha}$ and ent.-15-epi-7-thia PGF$_{1\alpha}$, which are also new compounds of the instant invention.

In addition to the foregoing, additional processes of this invention may be practised to obtain additional new final compounds of this invention. These additional processes may be represented by the following equations wherein the starting material is the cyclopentene oxide of Compounds I.

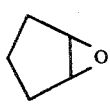

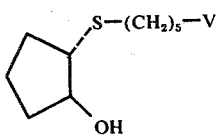

VIII
a. V=CH₂OH
b. V=COOH

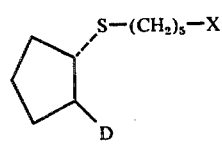

IX
a. X=COOH; D=Cl or Br
b. X=CH₂OSO₃CH₃; D=Cl or Br

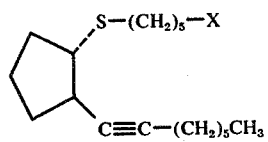

X
a. X=COOH
b. X=CH₂OH

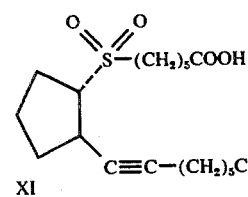

XI

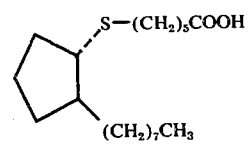

XII

In this alternate process the cyclopentene oxide of Compound I may first be converted to into the hydroxy acid of Compounds VIII, by treatment with an alkyl mercaptoalkanoate, for example, methyl 6-mercapto-n-hexanoate, or methyl 5-mercapto-n-pentanoate, and an alkali metal alkoxide, for example sodium methoxide, which are also new compounds of this invention. Alternatively, the cyclopentene epoxide may be treated with a mercapto alkanol, for example, 6-mercapto-1-hexanol, or 5-mercapto-1-pentanol, and an alkali metal alkoxide, for example, sodium methoxide, to yield the diol compound of Compounds VIII, which are also new compounds of this invention. Compounds VIII are then respectively converted to the halide derivatives by treatment with an alkane sulfonyl halide, for example, methanesulfonyl chloride, in a pyridine medium, to yield the respective Compounds IX, which are also new compounds of this invention. Compounds IX, wherein X=COOH may then be treated with an acetylenic reagent, for example, an alkynyl lithium, such as 1-octynyllithium, 1-heptynyllighium or 1-hexynyllithium, to yield the corresponding prostynoic acid of Compound X. The rac 7-thia-13-prostynoic acid of Compound X, has previously been reported in a previous publication of Fried et al., Advance Abstracts, International conference on Prostaglandins 1972. The halo sulfonate compound of Compounds IX, may be treated with an alkynyl lithium for example, octynyllithium or heptynyllithium, to yield the primary alcohol of Compound X, which is a new compound of this invention. These primary alcohol compounds of Compound X may then be converted to 7-thia-13-prostynoic acid by catalytic oxidation with platinum and oxygen.

In addition to the foregoing, the 7-thia-13-prostynoic compounds of this invention may be further processed to yield additional new compounds of this invention. The sulfone of 7-thia-13-prostynoic acid may be prepared by treatment of the methyl ester of the acid with sodium periodate and subsequent hydrolysis to yield the desired sulfone Compound XI, which are also new compounds of the instant invention. To obtain the 7-thiaprostanoic acid final products of this invention, the 7-thia-13-prostynoic acid of Compounds X are reduced as by treatment with palladium on charcoal in ethyl acetate to yield the saturated final compounds XII, which are also new products of the present invention.

In addition to the foregoing, further new final products may be prepared by the practise of this invention. These additional new products and the processes of their production may be represented by the following equations wherein the starting material are those of Compounds II, set forth hereinabove:

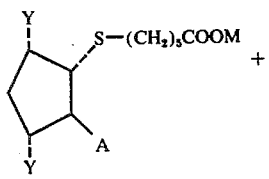

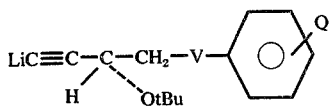

XIII
a. V=O; Q=Halogen
b. V=CH₂; Q=Halogen
c. V=O; Q=CF₃
d. V=CH₂; Q=CF₃

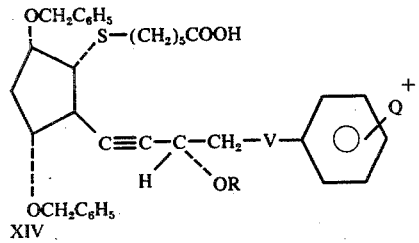

XIV

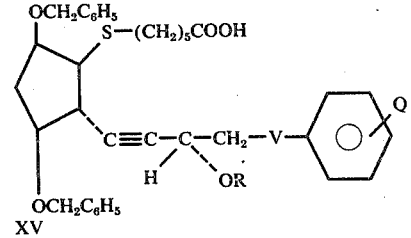

XV

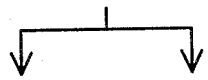

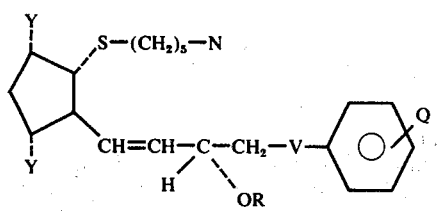

XVI
a. N=CH₂OH
b. N=COOH

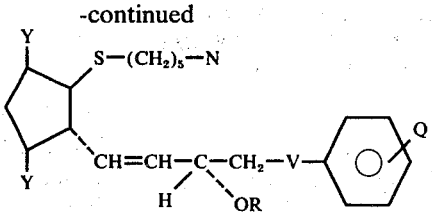

XVII
a. N=CH₂OH
b. N=COOH

In this alternate process, Compounds II are treated with an aromatically substituted alkoxy acetylenic reagent, Compounds XIII, to yield the aromatically substituted Compounds XIV and XV which are also new compounds of this invention. Compounds XIV and XV are then further treated in the same manner as Compounds III above, to yield compounds XVI and XVII, which are also new compounds of this invention. Similarly, other new compounds of this invention may be obtained by the further treatment of Compounds IX of this invention, by the above noted additional processes hereof. Thus, Compounds IX may be treated with the acetylenic reagent Compounds XIII to yields compounds of the formula

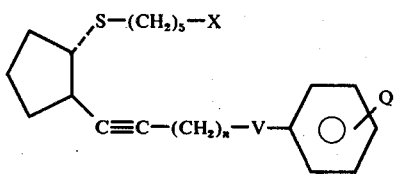

which may then be further treated in accordance with the processes hereinbefore set forth to obtain the aromatically substituted analogs of Compounds XI and XII.

The acetylenic reagent of Compounds XIII, i.e.

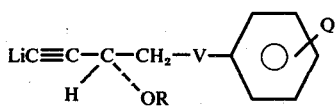

wherein R is lower alkyl, for example, butyl, propyl or pentyl; V is oxygen or $(CH_2)_n$, wherein $n$ is as defined above; and Q is a monovalent electronegative substituent occupying the meta or para position on the aromatic moiety, and is selected from the group consisting of halogens, such as chloro bromo or fluoro, and $CF_3$; may be prepared in accordance with the teaching set forth in my copending application Ser. No. 274365, filed July 24, 1972. Thus, the acetylenic reagents may be prepared by reacting an aldehyde of the formula:

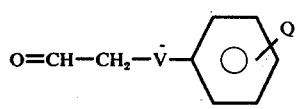

wherein V is oxygen or $(CH_2)_n$; and Q is halogen or $CF_3$, with a compound of the formula $HC \equiv CM_gBr$ and then further treating the resultant product to yield the desired reagent of Compounds XIII. Among the alkehyde compounds which may be employed in the practise of this invention are included substituted phenoxyacetaldehyde, for example para-fluorophenoxyacetaldehyde, or m-chloro-β-phenylpropionaldehyde, to yield the corresponding aryl-alkoxy-alkynyl lithium reagent, for example, 3-t-butoxy-4(p.-fluorophenoxy)-1-butynyl lithium; and 3-t-butoxy-5-(m-trifluoromethyl phenyl)-1-pentynyllithium. These reagents may then be further employed in the production of the compounds of this invention as aforesaid.

The invention may be illustrated by the following examples:

EXAMPLE I

Preparation of (±)-1,4-Dibenzyloxy-2-(1'-carboxymethyl-n-pentyl-5'-thio)-3-hydroxycyclopentane.

To a solution of methyl 6-mercapto-n-hexanoate (3.24 g, 20 mmoles) in 3 ml of dry methanol is added at 0° a solution of sodium methoxide (prepared from 1.08 g, 20 mmoles of sodium methoxide and 5 ml of dry methanol) dropwise with stirring under an atmosphere of nitrogen. The mixture is stirred for an additional 45 min at 25° when a very light brown solution is formed. To this solution is added a 0°, trans-dibenzyloxy epoxide, (2.96 g, 10 mmoles) in 4 ml of dry methanol with stirring. The reaction mixture is stirred for an additional 15 min at 25° and then allowed to reflux under a nitrogen atmosphere. After cooling, 5 ml of water is added with stirring at 0° over a 5 min period. The aqueous solution is acidified with 10% HCl to pH 3–4 at 0° and the solution extracted with ethyl acetate (3 × 50 ml). The organic layer is washed with water (2 ×10 ml), dried over anhydrous $MgSO_4$ and the solvent removed in a rotary evaporator under vacuum. The residue which is found to be partially hydrolyzed to the carboxylic acid is remethylated with diazomethane in ether to afford 5.2 g of a light yellowish brown viscous oil. This material is purified by alumina chromatography (activity IV) using 156 g of the adsorbant. Elution with hexane-benzene 1:4, and 2:3 eluted unchanged mercapto ester. The product was eluted with hexane-benzene 1:1, benzene and benzenechloroform 1:1 (3.47 g). Crystallization from etherhexane yields the pure product mp 37–39°. Anal. calcd for $C_{26}H_{34}O_5S$: C, 68.10; H, 7.47; S, 6.98. Found: C, 68.31; H, 7.51; S, 6.97.

Mass spectrum $M^+458$.

EXAMPLE 2.

Hydrolysis of (±)-1, 4-Dibenzyloxy-2-(1'-carboxymethyl-n-pentyl-5'-thio)-3hydroxycyclopentane.

Preparation of the Acid.

A solution of the methyl ester prepared according to Example 1 (2.05 g, 4.47 mmoles) in 5% methanolic KOH (33 ml, 30 mmoles, 6 mole equiv.) is allowed to stand at 25° for 16 hrs. Water (15 ml) is added, methanol is removed in vacuo and the residue is acidified at 0° with 10% hydrochloric acid to pH 3.4. The acidified solution is extracted with ethyl acetate (4×15 ml) and the organic layer washed with water (2×5 ml) dried over anhydrous magnesium sulfate and the solvent removed in vacuo. The residual crystalline material (1.98 g) after recrystallization from ethyl acetate/hexane furnished 1.77 g of the pure acid (87% yield) mp 66.5°–67°. Anal. calcd. for $C_{25}H_{32}O_5S$: C, 67.55; H, 7.26: S, 7.20. Found: C, 67.55; H, 7.31; S, 7.22.

Mass spectrum 445($M^+$+1).

EXAMPLE 3

Preparation of (±)-1,4-Dibenzyloxy-2-(1' carboxy-n-pentyl-5'-thio) -3-chlorocyclopentane.

To a solution of the acid, from Example 2,(2.22 g, 5 mmoles) in 10 ml of dry pyridine cooled to 0° is added methanesulfonyl chloride (3.435 g, 30 mmoles, 6 equiv.) through a dropping funnel over a 10 min period. The reaction is stirred at 0° under nitrogen for an additional 1½ hrs, after which 5 ml of ice water is added and the mixture is stirred for 5 min at 0°. The aqueous solution is then acidified with 10% hydrochloric acid at 0° to pH 3–4 and the acidified solution extracted with ethyl acetate (4×50 ml). The organic layer is washed with water (3×15 ml), dried over anhydrous magnesium sulfate and the solvent removed in vacuo. Excess pyridine is removed by evaporating toluene (2×10 ml) from the residue in vacuo and finally by drying under a high vacuum. There remained a viscous colorless material (2.30 g) of the chloro acid (99% yield). Anal. calcd for $C_{25}H_{31}O_4SCl$: C, 64.87; H, 6.70; S, 6.89; Cl, 7.67. Found: C, 65.83; H, 6.93S, 7.41; Cl, 7.42.

Mass spectrum of methyl ester: 477,479 ($M^+$ +1); 446,448 ($M^+$—$OCH_3$ +1).

EXAMPLE 4

Preparation of (±)-1, 4-Dibenzyloxy-2-(1'-carboxy-n-pentyl-5'-thio)-3-bromo-cyclopentane.

To a solution of the chloro acid from Example 3, (2.80 g, 6.31 mmoles) in 50 ml of dimethoxyethane (distilled, and dried over molecular sieves) is added granular lithium bromide (2.17 g, 25 mmoles, 4 equiv.). The resulting mixture is heated at 90°–95° (bath temperature) for 1½ hrs under nitrogen. It is cooled, taken up in 200 ml of ethyl acetate and acidified to pH 3–4 by the addition of a few drops of 10% HCl. The mixture is washed with brine (2 ×2 ml), dried over anhydrous $MgSO_4$ and the solvent removed in vacuo leaving a light brown viscous material (2.75 g, yield 86%) consisting of the bromo acid.

Mass spectrum of methyl ester: 520, 522($M^+$); 489,491 ($M^+$—$OCH_3$).

EXAMPLE 5

Preparation of 15-(S)-7-Thia-9α, 11α-dibenzyloxy-15-t-butoxy 13-prostynoic Acid.

To a solution of (S)-3-t-butoxy-1-octyne (2.912 g, 16 mmoles, 3 equiv.) in 30 ml of dry dimethoxyethane is added at 0° with stirring under nitrogen 9.5 ml of n-butyllithium (15.8 mmoles) in hexane. The mixture is stirred for an additional 30 min.

The above reagent is then added to a solution of the sodium salt of the bromo acid from Example 4 prepared as follows: 528 Milligrams of a 50% suspension of sodium hydride in mineral oil (11 mmoles, 2 equiv.) is washed twice with hexane and dried under nitrogen to form a fine powder. This dry powder is suspended in 1 ml of dry toluene and there is added the solution of the bromo acid in 8 ml of dry toluene at 0° slowly with stirring. The reaction is allowed to proceed at that temperature until hydrogen evolution ceases. To this mixture is added the above solution of (S)-3-t-butoxy-1-octynyllithium in dimethoxyethane at 0° with stirring over a 10 min period. The resulting reaction mixture is allowed to stir at 25° for 24 hrs under nitrogen, when a light brown colored solution is formed. The latter is cooled to 0° and after the slow addition of 5 ml of water is stirred for 5 min. After acidification with 10% HCl to pH 3–4 followed by extraction with ethyl acetate (3 ×15 ml) the organic layer is washed with water, dried over anhydrous $MgSO_4$, and the solvents removed in vacuo to give 4.77 g of crude product. This material is purified by chromatography over silica gel (300 g) and eluted with 10% benzene in ethyl acetate and 25% benzene in ethyl acetate which removed the t-butoxyoctyne. The desired product was eluted with benzene-ethyl acetate 1:1 and ethyl acetate to furnish 1.08 g (33% yield) of the 15-(S)-7-thia-9α, 11α-dibenzyloxy-15-t-butoxy-13-prostynoic acid $[\alpha]_D^{CHCL_3} - 18.6°$ (c, 6.2).

Anal. calcd. for $C_{27}H_{52}O_5S$: C, 72.99; H, 8.61; S, 5.26. Found: C, 72.77; H, 8.54; S, 5.09.

Mass spectrum of methyl ester: 569($M^+$—57 [$CCH_3$]$_3$).

EXAMPLE 6

Preparation of 15-(S)-7-Thia-9α, 11α-dibenzyloxy-15-hydroxy-13-prostynoic Acid Methyl Ester A solution of 930 mg of the t-butoxy acid from Example 5, in 5 ml of methanol is treated with excess ethereal diazomethane for 20 min. After removal of the solvents in vacuo the residue is dissolved in 8 ml of anhydrous trifluoroacetic acid and the mixture stirred at 0° for 2 hrs. It is then taken up in 100 ml of ethyl acetate washed with water (2×10 ml), 10% $NaHCO_3$ solution (3×10 ml), dried over magnesium sulfate and the solvent removed in vacuo. The resulting residue is allowed to stand with 20 ml of a solution of $K_2CO_3$ in 50% aqueous methanol for 30 min at 25°. After removal of the methanol in vacuo the aqueous residue is acidified with 10% hydrochloric acid at 0° to pH 4 and the mixture extracted with ethyl acetate. The ethyl acetate extract is washed with water to neutrality, dried over anhydrous magnesium sulfate and the solvent removed to yield 830 mg of crude material. This was purified by column chromatography on 64 g of silica gel to afford 178mg of the pure 15-(S)-7-thia-9α,11α- dibenzyloxy-15-hydroxy-13-prostynoic acid methyl ester. $[\alpha]_D^{CHCl_3} - 1.4°$ (c, 1.3)

Mass spectrum of 15-trimethylsilyl ether: 567 ($M^+ +1$).

EXAMPLE 7

Lithium Aluminum Hydride Reduction of 15-(S)-Thia-9 α, 11α-dibenzyloxy-15-hydroxy-13-prostynoic Acid Methyl Ester.

To a solution of the 7-thia-prostynoic acid methyl ester from Example 6, (150 mg, .265 mmoles) in 10 ml of anhydrous THF is added dropwise with stirring under nitrogen a solution of 152 mg of lithium aluminum hydride (4 mmoles) in 10 ml of anhydrous THF. The reaction mixture is kept at 0° for an additional 10 min, allowed to warm to room temperature and then heated at 70°-75° bath temperature for 3 hrs under nitrogen. It is cooled to 0° and excess lithium aluminum hydride is destroyed by dropwise addition of a saturated solution of sodium potassium tartrate. The resulting mixture is extracted with ethyl acetate (4×50 ml), the organic layer washed with 5 ml of brine and dried over anhydrous magnesium sulfate. After removal of the solvent 145 mg of crude product was obtained, which consisted of a mixture of the two diastereomeric alcohols IVa and Va. These were separated by preparative thin layer chromatography on silica gel (6 20 ×20 plates, 250 microns) using benzene-ether 3:2 to develop the plates (3 passes). The fastest moving fraction (29 mg) consisted of the alcohol (IVa) which after crystallization from ethyl acetate-hexane had mp 62° − 64° $[\alpha]_D^{CHCl_3} + 25.9°$ (c, 2.9).

Mass spectrum: 523 ($M^+$−17).

This was followed by a second band consisting of the diastereomeric alcohol (Va) (43 mg). Mp 52°-54° after crystallization from ethyl acetate-hexane; $[\alpha]_D^{CHCl_3} - 17.1°$ (c, 2.20).

The diastereomer (Va) was analyzed. Anal. calcd for $C_{33}H_{48}O_4S$. C, 73.30; H, 8.95; S, 5.90. Found: C, 73.16; H, 8.86; S, 5.69.

EXAMPLE 8

Debenzylation of the Alcohol (IVa).

Preparation of nat-15-(S)-7 Thia-1, 9α, 11α, 15-tetrahydroxy-13-prostene.

To sodium hydride powder prepared from 18 mg of a 50% oil suspension (5 equiv.), which had been washed twice with hexane under nitrogen and dried, is added at 25° a solution of the dibenzyl ether (IVa) (29 mg, .0537 mmoles) in 4 ml of anhydrous THF (distilled over lithium aluminum hydride and dried over molecular sieves). The resulting solution of the sodium salt of IVa is stirred at the same temperature for 30 min and 20 ml of ammonia (dried over lithium for 15 min) is distilled into the flask containing the sodium salt solution, which is equipped with a dry ice-acetone reflux condenser. The mixture is cooled to −78° and very small pieces of lithium are added with stirring until the blue color which at first disappears after 5-10 min remains constant. The temperature is maintained at −78° throughout and the reaction is allowed to proceed for 3½ hours. Ammonium chloride is then added to neutralize the mixture and the ammonia and tetrahydrofuran allowed to evaporate at room temperature with the aid of nitrogen. The residue is acidified with 10% HCl to pH 3-4 at 0°. After saturating with sodium chloride the residue is thoroughly extracted with ethyl acetate (4×50 ml) and the organic layer washed once with brine and dried over anhydrous magnesium sulfate. Removal of the solvent leaves 18.7 mg of crude tetrol (IVb) which after column chromatography on silica gel and crystallization from ethyl acetate-hexane afforded 12 mg (63& yield) of the pure tetrol, mp 99 − 100°; $[\alpha]_D^{CHCl_3} + 11.2°$ (c, .9); $[\alpha]^{MeOH} + 11.2$ (c,1.2).

Mass spectrum of the tetra-trimethylsilyl ether: 649($M^+ +1$).

EXAMPLE 9

Debenzylation of the Alcohol Va.

Preparation of the Enantiomer of 15-7-Thia-1, 9α, 11α-15-epi-tetrahydroxy-13-prostene.

Following the procedure of Example 8 but substituting an equal amount of the diastereomeric dibenzyl ether (Va) for the dibenzyl ether (IVa) used in the previous example there is obtained 12 mg (50% yield) of the diastereomeric tetrol, which could not be induced to crystallize. $[\alpha]_D^{CHCl_3} - 6.0°$ (c, .4) $[\alpha]_D^{EtOH} - 3.6°$ (c, 1.9). Mass spectrum of the tetra-trimethylsilyl ether: 649($M^+ +1$).

EXAMPLE 10

7-Thia-$PGF_{1\alpha}$ (nat-15-(S)-7-Thia-9α, 11α-15-trihydroxy-13-prostene-1-oic Acid).

Into a 25 ml 3-neck flask containing a magnetic stirrer and provided with a reflux condenser is placed 100 mg of platinum oxide (Engelhart) and 3 ml of distilled water. The flask is evacuated and refilled with nitrogen twice and the catalyst is reduced with hydrogen for 20 min at which time it has coagulated. The flask is evacuated again flushed with nitrogen and finally oxygen is bubbled through the solution via a syringe needle for 5 min. 25 Milligrams of sodium bicarbonate (.3 mmoles) is then added, followed by a solution of the tetrol (IVb) (11 mg, .031 mmoles) in water-acetone (1.5 ml, 3:1). The vessel from which the tetrol was added is rinsed with .2 ml of acetone and .5 ml of water-acetone (3:1) and these washings added to the mixture. Oxygen is then bubbled through the solution and the flask is heated at a bath temperature of 55°, water-acetone (.5 ml, 3:1) being added every 45 min to replace evaporated solvent. The reaction is continued for 3 hrs, after which an aliquot is checked by the tlc for completion of the reaction. When complete the reaction mixture is centrifuged, the clear yellow supernate evaporated in vacuo, and acidified at 0° with 10% hydrochloric acid to a pH of 3-4. The mixture is then saturated with sodium chloride and extracted with ethyl acetate (4×25 ml). The organic layer is washed with brine (1 ml) dried over anhydrous magnesium sulfate and the solvent is removed in vacuo to furnish 11 mg of the crude 7-thiaprostaglandin $F_1$. The crude product was purified via high pressure chromatography on silica gel using 1.6 g of adsorbant. The pure acid VI (5 mg) was isolated from the ethyl acetate −10% methanol eluates. It had the following properties: mp 94°-96°; $[\alpha]_D^{MeOH}$ 5.5° (c, .43); $[\alpha]_D^{THF}$ +12°(c, .17).

Mass spectrum of the methyl ester tris-trimethylsilyl ether 604 ($M^+$) strong.

EXAMPLE 11

Preparation of the Enantiomer of 7-Thia-9α, 11α-15-epi-trihydroxy-13-prostene-1-oic Acid.

Following the procedure of Example 10 but substituting an equal amount of the enantiomer of 7-thia,-1, 9α, 11α, 15-epitetrahydroxy-13-prostene for the tetrol IVb there is obtained the enantiomer of 15-epi-7-thia PGF$_{1\alpha}$ which could not be induced to crystallization $[\alpha]_D^{CHCl_3} - 4.4°$ (c, .27).

Mass spectrum of the methyl ester tris-trimethylsilyl ether 604 (M$^+$) strong.

EXAMPLE 12

Preparation of trans-2-(1'-carboxymethyl-n-pentyl-5'-thio)-cyclopentanol Methyl ester.

To neat methyl 6-mercapto-n-hexanoate (770 mg, 4.1 mmoles) is added with stirring at 0° under nitrogen a solution of sodium methoxide (221 mg, 4.1 mmoles) in 1 ml of absolute methanol. The addition requires 10 min, after which time the mixture is stirred at 0° for an additional 30 min, following which a solution of excess cyclopentene oxide (Ia) (420 mg, 5.0 mmoles) in 1 ml of methanol is added at 0° over a 5 min period. The reaction mixture is stirred at 0° for an additional 30 min and then at 25° for 5 hrs, all under an atmosphere of nitrogen. Water (5 ml) is then added and the solution acidified with 10% H$_2$SO$_4$ to pH 3–4. The acidified solution is extracted with ethyl acetate (4×50 ml) and the organic layer washed with water, dried over anhydrous magnesium sulfate and the solvent removed in vacuo. The colorless viscous material is kept in high vacuum overnight to remove excess cyclopentene oxide. The resulting thio methyl ester (966 mg) is used in the next step without further purification.

EXAMPLE 13

Preparation of (±)-trans-2-(1'-Carboxy-n-pentyl-5'-thio)-cyclopentanol.

A solution of the methyl ester prepared in Example 12 (955 mg, 3.80 mmoles) in 33 ml of 2% methanolic KOH is stirred at 25° for 20 hrs. Water is added, the methanol is removed in vacuo and the aqueous residue is acidified with HCl to pH 3–4 at 0°. The resulting solution is extracted with ethyl acetate (4×50 ml), washed twice with water, dried over anhydrous magnesium sulfate and the solvent removed in vacuo. There remained a colorless viscous material (862 mg, yield 98%) which consists of the pure acid (VIIIb). Anal. calcd. for C$_{11}$H$_{20}$O$_3$S. C, 56.88; H, 8.68; S, 13.78. Found: C, 56.19; H, 8.67; S, 13.17.

Mass spectrum: 246 (M$^+$).

EXAMPLE 14

Preparation of (±)-trans-1'-Carboxy-n-pentyl-5'-thio)-2-chlorocyclopentane.

To a solution of the hydroxy acid from Example 13, (580 mg, 2.5 mmoles) in 10 ml of dry pyridine cooled to 0° is added methanesulfonyl chloride (860 mg, 7.5 mmoles) dropwise over a 5 min period. The reaction is stirred for 1 hr at 0° under nitrogen following which it is poured into a solution of ice cold brine containing hydrochloric acid sufficient to render the mixture acidic. The acidified solution is extracted with ethyl acetate (4×50 ml) and the ethyl acetate extract backwashed with 10% hydrochloric acid, brine and water. The ethyl acetate extract is then dried over anhydrous magnesium sulfate and the solvent removed in vacuo. Yield of (IXa) 82%. Anal. calcd for C$_{11}$H$_{19}$O$_2$SCl. C, 52.68; H, 7.62; S, 12.76; Cl, 13.99. Found: C, 52.75; H, 7.76; S, 12.91; Cl, 13.61.

Mass spectrum: 250, 252 (M$^+$).

EXAMPLE 15

Preparation of (±)-trans-(1'-Carboxy-n-pentyl-5'-thio)-2-bromocyclopentane.

To a solution of the chloro acid from Example 14, (1.20 g, 4.8 mmoles) in 8 ml of dry dimethoxyethane is added solid lithium bromide (1.20 g, 14 mmoles, 3 equiv.). The reaction mixture is refluxed for 30 min, cooled, and poured into 15 ml of ice water. The resulting mixture is extracted with ethyl acetate (3×50 ml) and the organic layer washed with water, dried over anhydrous magnesium sulfate and freed from solvent in vacuo. The dark-brown residue (1.10g) consists of the bromo acid (yield 78%).

Mass spectrum: 294, 296 (M$^+$).

EXAMPLE 16

Preparation of (±)-7-Thia-13-prostynoic Acid.

Octynyllithium is prepared as follows: To a solution of 1-octyne (550 mg, 5 mmoles) in 15 ml of dry dimethoxyethane (dried first over calcium hydride followed by distillation over lithium aluminum hydride) is added at 0° with stirring under nitrogen 3.24 ml (5 mmoles) of n-butyllithium in hexane. The mixture is stirred for an additional 30 min and the resulting solution of octynyllithium added to a solution of the sodium salt prepared from the chloro acid of Example 14 as follows: 96 Milligrams of a 50% suspension of sodium hydride in mineral oil is washed twice with hexane and dried under nitrogen. The resulting powder is suspended in 1 ml of dry toluene and to it is added the chloro acid (238 mg, .94 mmole) in 3 ml of dry toluene with stirring under nitrogen. The mixture is stirred for an additional 10 min at 25° under nitrogen which results in the formation of a thick slurry of the sodium salt of the chloro acid. To this slurry is added the octynyllithium reagent prepared above and the mixture maintained at 25° for 10 min, which results in the formation of a solution. The reaction mixture is heated at reflux (bath temperature 95°–100°) for 1 hr under nitrogen, cooled and acidified with 10% HCl to pH 2–3. The acidified solution is extracted with ethyl acetate (3×30 ml) and the organic layer washed with water, dried over anhydrous magnesium sulfate and the solvent removed in vacuo. The resulting viscous residue (290 mg) is purified by chromatography on silica gel (11.6 g). The essentially pure thiaprostynoic acid is eluted with chloroform-benzene (1:1), pure chloroform and chloroform containing 20% ethyl acetate. The resulting material is further purified by high pressure chromatography on 26 g of silica gel using ethyl acetatehexane (4:1) as the eluent. Anal. calcd for C$_{19}$H$_{32}$O$_2$S. C, 70.33; H, 9.94. Found: C, 70.12; H, 9.97.

Mass spectrum of the acid: 324(M$^+$). Mass spectrum of the methyl ester (prepared with diazomethane): 338(M$^+$).

EXAMPLE 17

Preparation of (±)-7-Thia-13-prostynoic Acid.

Following the procedure of the previous example but substituting an equivalent amount of the bromo acid prepared in Example 15 for the chloro acid there is obtained 7-thia-13-prostynoic acid.

EXAMPLE 18

Preparation of the Sulfone of 7-Thia-13-prostynoic Acid.

13-Thia prostynoic acid (12 mg) is methylated in ether solution with diazomethane until the yellow color persists. Removal of the solvent furnishes 7thia-13-prostynoic acid methyl ester (12 mg). To a solution of the above methyl ester in 2 ml of methylene chloride is added m-chloroperbenzoic acid (35 mg, 4 equiv.) and the mixture stirred at 25° for 2 hrs. It is then diluted with more methylene chloride, washed successively with 10% aqueous sodium sulfite, 10% sodium bicarbonate and water until neutral, dried over anhydrous magnesium sulfate and the solvent evaporated in vacuo leaving 5 mg of the sulfone methyl ester.

The latter is hydrolyzed with .5 ml of 5% methanolic KOH solution at 25° for 16 hrs. Water is added, the methanol removed in vacuo and the solution acidified with 10% HCl to pH 2–3. The acidified solution is extracted with ethyl acetate (3×10 ml), washed with brine, dried over anhydrous magnesium sulfate and the solvent removed in vacuo, leaving 3.5 mg of the sulfone.

EXAMPLE 19

Preparation of 7-Thiaprostanoic Acid.

To a suspension of 50 mg of 10% palladium on charcoal in 1 ml of ethyl acetate, which had been prereduced with hydrogen gas was added 7-thia-13-prostynoic acid (15 mg) in 1.5 ml of ethyl acetate. After 5 hrs the catalyst was removed by filtration washed with ethyl acetate and the combined filtrates evaporated to yield 13 mg of a semisolid. Analysis by nmr indicated that there still remained starting material plus some 7-thia-13-cis-prostenoic acid. The material was therefore reduced again with 50 mg of fresh palladium catalyst for ½ hour and the reduced material isolated by filtration and removal of the solvent. 8 Milligrams of the saturated acid was obtained, which after recrystallization from hexane melted at 40°–41°.

Mass spectrum: 328 (M$^+$).

EXAMPLE 20

Preparation of 6-Mercapto-1-hexanol.

a. Preparation of aqueous sodium trithiocarbonate.

Sodium sulfide (Na$_2$S.9H$_2$O(M.W.240)24g) is dissolved in 50 ml of water with slight warming. To this solution is added carbon disulfide (8.36 g, .11 mmole) and the reaction mixture is warmed to 40° and allowed to stir for 6 hrs. The excess carbon disulfide is removed by evaporation at reduced pressure and the resulting deep-red liquid diluted to 60 ml with water to afford a 33% solution of sodium trithiocarbonate.

b. Preparation of 6-mercapto-1-hexanol.

A solution of 6-chloro-1-hexanol (4.08 g, 30 mmoles) in 10 ml of ethanol is added dropwise to 30 ml (50 mmoles) of the solution of sodium tricarbonate prepared under a) at 25°. The reaction mixture is heated at 60° for 2 hrs, cooled to 0° and acidified with 10% H$_2$SO$_4$. The acidified aqueous solution is extracted 3 times with ether and the ether layer washed with water, dried over anhydrous magnesium sulfate and the solvent removed in vacuo. The residue (6.5 g) on distillation in vacuo furnished 1.35 g (34%) of 6-mercapto-1-hexanol. Bp$_{4\ Torr}$ 78°–80°.

EXAMPLE 21

Preparation of trans-2-(1'-Hydroxy-n-hexyl-6'-thio)-cyclopentanol.

Following the procedure of Example 12 but substituting an equivalent amount of 6-mercapto-1-hexanol for the 6-mercapto-n-hexanoate there is obtained the diol (VIIIa). Anal. calcd for $C_{11}H_{22}O_2S$. C, 60.52; H, 10.16; S, 14.66. Found: C, 60.45; H, 10.19; S, 14.58.

Mass spectrum: 218 (M$^+$).

EXAMPLE 22

Preparation of trans-2-(1'-methanesulfonyloxy-n-hexyl-6'-thio)-chlorocyclopentane.

Following the procedure of Example 14 but substituting an equivalent amount of the diol (VIIIa) for the hydroxy acid there is isolated the chloro methanesulfonate (IXb). Anal. calcd for $C_{12}H_{23}O_3S_2Cl$. C, 45.76; H., 7.36; S, 20.35; Cl, 11.27. Found: C, 45.64; H, 7.41; S, 20.16; Cl, 11.34.

Mass spectrum: 314, 316 (M$^+$).

EXAMPLE 23

Preparation of (±)-7-Thia-13-prostyne-1-ol.

Following the procedure of Example 16 but substituting an equivalent amount of the chloro methanesulfonate for the sodium salt of the chloro acid there is obtained 7-thia-13-prostyne-1-ol. Anal. calcd for $C_{19}H_{34}OS$. C, 73.50; H, 11.04; S, 10.30. Found: C, 73.29; H, 10.96; S, 10.58.

Mass spectrum: 310 (M$^+$).

EXAMPLE 24

Preparation of (±)-7-Thia-13-prostynoic Acid.

Following the procedure of Example 10 but substituting an equivalent amount of 7-thia-13-prostyne-1-ol for the tetrol there is obtained (±)-7-thia-13prostynoic acid.

EXAMPLE 25

Following the procedures set forth in Examples VII through XI of my copending application, Serial No. 274365, filed July 24, 1972, but substituting equivalent amounts of m-chlorophenylpropionaldehyde, or p-fluorophenoxyacetaldehyde for 3-hexen-1-al, there is obtained 3-t-butoxy-5-(m-chlorophenyl)-1-pentyne, and 3-t-butoxy-4-(p-fluorophenoxy)-1-butyne.

Following the procedure set forth in Example 5 hereinabove, but substituting equivalent amounts of 3-t-butoxy-5-(m-chlorophenyl)-1-pentyne, or 3-t-butoxy-4-(p-fluorophenoxy)-1-butyne for 3-t-butoxy-1-octyne, there is obtained the respective chlorophenyl and fluorophenoxy analogs of 7-thia-9,11-dibenzyloxy-15-t-butoxy-13-prostynoic acid.

The respective chlorophenyl and fluorophenoxy analogs may then be further treated in accordance with the subsequent examples of this invention to yield the respective chlorophenyl and fluorophenoxy analogs of this invention.

The invention may be variously otherwise embodied within the scope of the appended claims.

What is claimed is:

1. A compound of the formula:

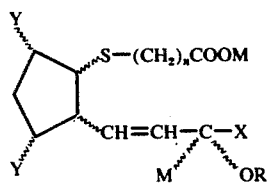

wherein
M is H, or lower alkyl;
Y is OH, acyloxy, or lower alkoxy;
X is lower alkyl;
R is H, acyl, or lower alkyl;
$n$ is an integer from 2 to 5; and
wherein the acyl radicals are derived from hydrocarbon carboxylic acids of 12 carbon atoms or less.

2. A compound of the formula:

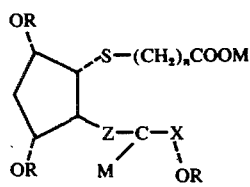

or

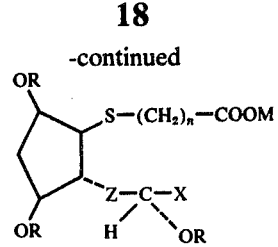

wherein
Z is CH=CH; and
R, $n$, M and X are as defined in claim 1.

3. A compound of the formula:

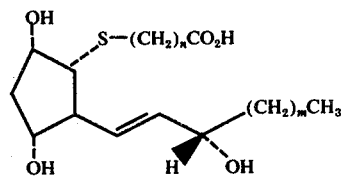

wherein
$n$ is 4 or 5,
$m$ is 4 or 5.

4. A compound of the formula:

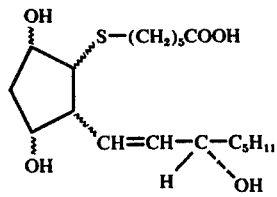

* * * * *